United States Patent
Liang et al.

(10) Patent No.: US 10,487,094 B1
(45) Date of Patent: Nov. 26, 2019

(54) BERGENIN THIODIPROPIONIC ACID ESTER WITH ANTIOXIDANT ACTIVITY AND A METHOD OF IMPROVING THE ANTIOXIDANT PROPERTY OF GANODERMA LUCIDUM SPORE OIL USING THE SAME

(71) Applicants: Chengyuan Liang, Xi'an (CN); Yuzhi Liu, Xi'an (CN); Danni Tian, Xi'an (CN); Jie Li, Xi'an (CN); Songsong Ruan, Xi'an (CN); Han Li, Xi'an (CN); Qianqian Zhao, Xi'an (CN); Xuechuan Wang, Xi'an (CN); Xeufeng Chen, Xi'an (CN)

(72) Inventors: Chengyuan Liang, Xi'an (CN); Yuzhi Liu, Xi'an (CN); Danni Tian, Xi'an (CN); Jie Li, Xi'an (CN); Songsong Ruan, Xi'an (CN); Han Li, Xi'an (CN); Qianqian Zhao, Xi'an (CN); Xuechuan Wang, Xi'an (CN); Xeufeng Chen, Xi'an (CN)

(73) Assignee: SHAANXI UNIVERSITY OF SCIENCE AND TECHNOLOGY, Xi'an (CN)

(*) Notice: Subject to any disclaimer, the term of this patent is extended or adjusted under 35 U.S.C. 154(b) by 0 days.

(21) Appl. No.: 16/120,406

(22) Filed: Sep. 3, 2018

(51) Int. Cl.
  *C07D 519/00* (2006.01)
  *C09K 15/12* (2006.01)

(52) U.S. Cl.
  CPC ............ *C07D 519/00* (2013.01); *C09K 15/12* (2013.01)

(58) Field of Classification Search
  CPC ............................ C07D 519/282; C09K 15/12

USPC .......................................................... 549/282
See application file for complete search history.

(56) References Cited

FOREIGN PATENT DOCUMENTS

CN        108997379 A    *   12/2018   ......... C07D 519/00

OTHER PUBLICATIONS

Abstract , Final safety assessment of thiodipropionic acid and its dialkyl esters as used in cosmetics. Diamante C. et al (Year: 2010).*

* cited by examiner

Primary Examiner — Rita J Desai

(57) ABSTRACT

A compound having the following formula (I):

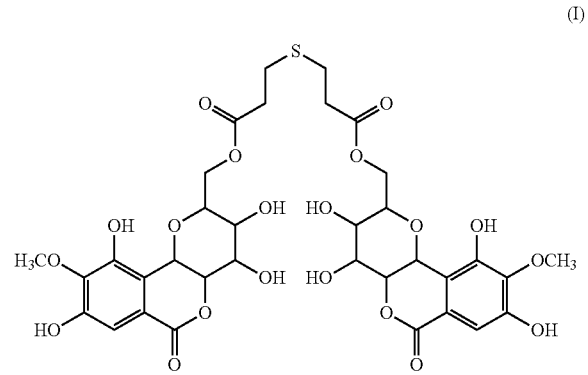

is disclosed. A method of preparing the compound of formula (I) is also disclosed.

12 Claims, 1 Drawing Sheet

BERGENIN THIODIPROPIONIC ACID ESTER WITH ANTIOXIDANT ACTIVITY AND A METHOD OF IMPROVING THE ANTIOXIDANT PROPERTY OF GANODERMA LUCIDUM SPORE OIL USING THE SAME

The present invention claims priority to Chinese Patent Application No. CN 201810649370.6, filed on Jun. 22, 2018, which is incorporated by reference for all purposes as if fully set forth herein.

FIELD OF THE INVENTION

The present invention relates to medical chemistry, in particular, to a bergenin thiodipripionic acid ester with antioxidant activity and a method of improving the antioxidant property of Ganoderma lucidum spore oil using the same.

BACKGROUND OF THE INVENTION

Bergenin (compound of formula II), also known as dwarf tea, was first published in the "Plant Name Map," which is a lactone formed by methyl gallic acid C-glucoside, usually white loose needle crystal or crystalline powder, and its plant source is mainly distributed in Yunnan, Sichuan, Tibet and other provinces in China. A large number of clinical trials have also confirmed that bergenin has anti-inflammatory analgesic, antitussive and antiasthmatic effects, and is often used as an effective component of cough and anti-inflammatory drugs in the treatment of cough, acute and chronic bronchitis, duodenal ulcer and the like. At present, bergenin tablets have been used as medicines for the treatment of chronic bronchitis. Recently, many pharmacological experiments have shown that bergenin has a variety of biological activities, including liver protection, anti-ulcer, improve immunity, anti-lipid oxidation and free radical scavenging. It was found that bergenin could effectively inhibit the lipid peroxidation stress in brain tissue after ischemia by inhibiting the increase of lipid peroxidation content in mouse brain tissue caused by ischemia/reperfusion injury. At the same time, the superoxide anion radical generated by the xanthine-xanthine oxidase system also has obvious scavenging effect. It is believed that bergenin has anti-lipid oxidation effect and it can be used as a new food additive for the production of vegetable oil to extend the shelf life of vegetable oil.

Thiodipropionic acid (cas: 111-17-1; compound of formula III) is a common antioxidant used in the industry to produce thioester antioxidants. A large number of studies shows that antioxidants are an important step in preventing aging, because free radicals or oxidants break down cells and tissues to affect metabolic functions, causing a variety of health problems. If excessive oxidative free radicals can be eliminated, many free radical-induced and aging-related diseases can be prevented.

In the present invention, structural modification of bergenin using thiodipropionic acid to obtain a sulfur-containing bergenin derivative. The antioxidant activity of the compound was verified by anti-oxidation experiments.

SUMMARY OF THE INVENTION

In one embodiment, the present invention provides a compound (bergenin thiodipripionic acid ester) having the following formula (I).

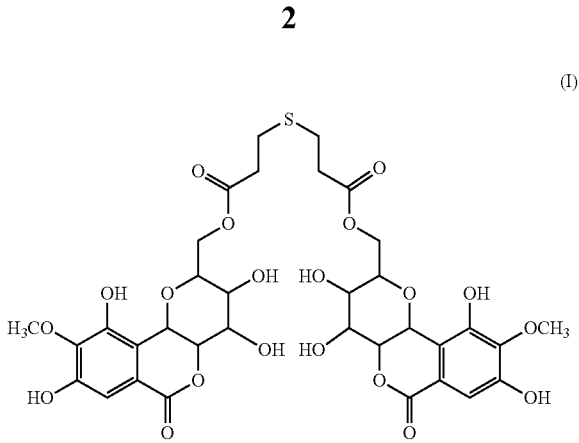

In one embodiment, the present invention provides a method of preparing the compound of formula (I). The method includes reacting the compound of formula (II) with the compound of formula (III) to obtain the compound of formula (I):

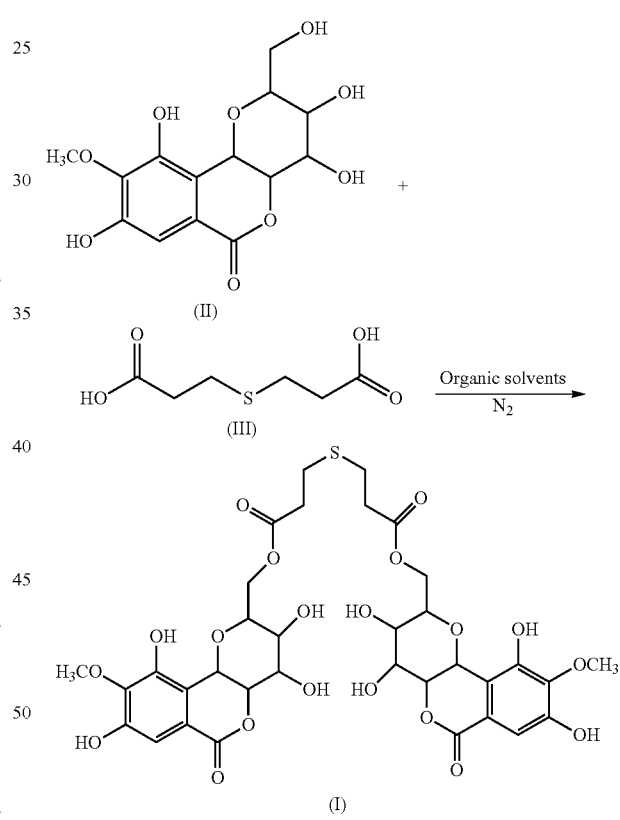

In another embodiment, the reaction of the compound of formula (II) with the compound of formula (III) includes the following steps: placing the compound of formula (II) and the compound of formula (III), in a molar ratio of 2:1 to 2.2:1, in a reactor under nitrogen atmosphere to obtain a reaction mixture; adding an organic solvent and a certain amount of a dehydrating agent to the reaction mixture under magnetic stirring; heating the reaction mixture at 50-60° C. for 15-17 hours; concentrating the reaction mixture to obtain crude compound of the formula (I); and using a macroporous resin to purify the crude compound of the formula (I) to obtain the compound of formula (I).

In another embodiment, the organic solvent is acetonitrile or THF.

In another embodiment, the organic solvent is acetonitrile.

In another embodiment, the molar ratio of the compound of formula (II) and the compound of formula (III) is 2.2:1.

In another embodiment, the dehydrating agent is N,N'-dicyclohexylcarbodiimide (DCC), 1-ethyl-3-(3-dimethylaminopropyl)carbodiimide (EDC), or sulfuric acid.

In another embodiment, the dehydrating agent is EDC.

In another embodiment, the reaction mixture is heated at 60° C.

In another embodiment, the reaction mixture is heated for 16 hours.

In another embodiment, the macroporous resin is an AB-8 type polar macroporous resin, an S-8 type polar macroporous resin, or an ADS-2 type polar macroporous resin.

In another embodiment, the macroporous resin is an AB-8 type polar macroporous resin.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENT

Figure 1:
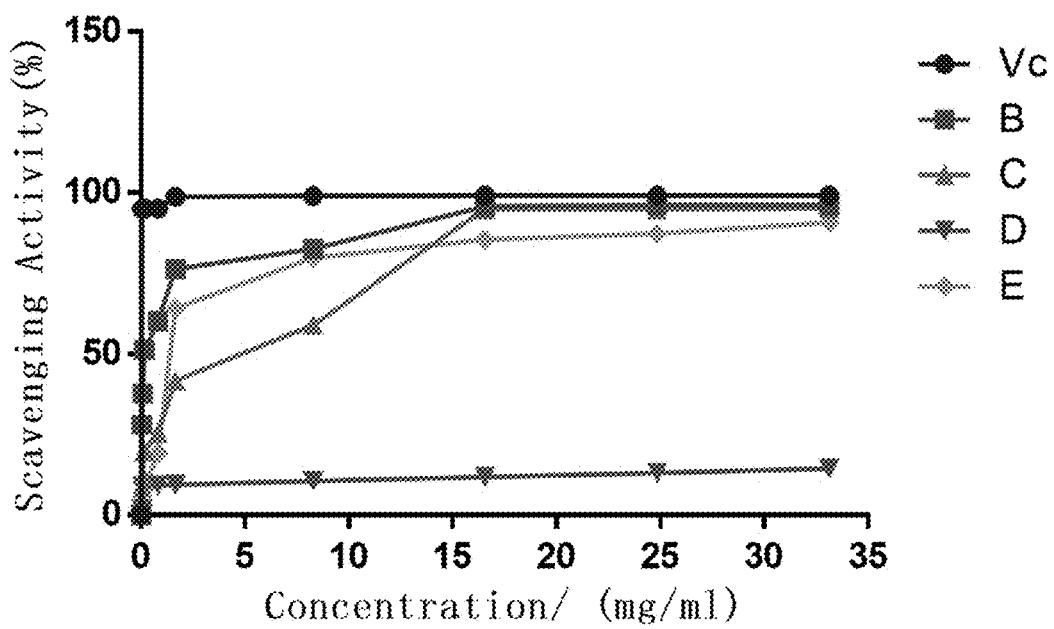
FIG. 1 shows the scavenging activity of the samples Vc, B, C, D, and D at different concentrations.

Reference will now be made in detail to embodiments of the present invention, example of which is illustrated in the accompanying drawings. The following examples illustrate the present invention, but the present invention is not limited to the following examples.

Example 1

Preparation of Bergenin Thiodipripionic acid ester (bis((3,4,8,10-tetrahydroxy-9-methoxy-6-oxo-2,3,4,4a,6,10b-hexahydropyrano[3,2-c]isochromen-2-yl)methyl) 3,3'-thiodipropionate) (the compound of formula (I))

233 mg (0.71 mmol) bergenin and 60 mg (0.34 mmol) of thiodipropionic acid, a molar ratio of 2.1:1, were placed in a 100 mL reactor. 40 mL acetonitrile was added to form a reaction mixture under nitrogen atmosphere. A catalytic amount of dehydrating agent EDC was added to the reaction system under magnetic stirring, and the reaction mixture was heated at 60° C. for 16 hours. When TLC indicated that the reaction was complete, heating was stopped and the protective device was removed. The reaction mixture was then concentrated under reduced pressure, and the concentrate was allowed to stand for stratification. The organic phase of the concentrated mixture was collected to obtain crude bergenin thiodipripionic acid ester. The crude product was further purified by using macroporous resin AB-8 and methanol as an eluent. The eluent was repeatedly eluted, dried over anhydrous sodium sulfate, and s concentrated under reduced pressure to obtain 144 mg bergenin thiodipripionic acid ester, a yield of 52.9%.

$^1$H-NMR (400 MHz, DMSO-d$^6$) δ (ppm): 9.37 (2H, s), 9.24 (2H, s), 6.89 (2H, s), 5.47 (2H, d), 5.01 (2H, m), 4.41-4.23 (6H, m), 4.10-3.95 (6H, m), 3.57 (6H, s), 3.34 (2H, m), 2.48 (4H, t), 2.35 (4H, t); $^{13}$C-NMR (75 MHz, DMSO-d$^6$) δ (ppm): 165.1, 160.5, 143.2, 140.4, 139.5, 119.8, 111.7, 103.2, 75.2, 73.5, 69.9, 68.7, 65.9, 57.1, 53.8, 27.5, 22.6; MS (ESI) for (M+H)+: 799.7.

Example 2

Preparation of Bergenin Thiodipripionic Acid Ester 338 mg (1.03 mmol) bergenin and 87 mg (0.49 mmol) of thiodipropionic acid, a molar ratio of 2.1:1, were placed in a 100 mL reactor. 40 mL acetonitrile was added to form a reaction mixture under nitrogen atmosphere. A catalytic amount of dehydrating agent DCC was added to the reaction system under magnetic stirring, and the reaction mixture was heated at 60° C. for 16 hours. When TLC indicated that the reaction was complete, heating was stopped and the protective device was removed. The reaction mixture was then concentrated under reduced pressure, and the concentrate was allowed to stand for stratification. The organic phase of the concentrated mixture was collected to obtain crude bergenin thiodipripionic acid ester. The crude product was further purified by using macroporous resin AB-8 and methanol as an eluent. The eluent was repeatedly eluted, dried over anhydrous sodium sulfate, and s concentrated under reduced pressure to obtain 137.8 mg bergenin thiodipripionic acid ester, a yield of 35.2%.

Example 3

Preparation of Bergenin Thiodipripionic Acid Ester 233 mg (0.71 mmol) bergenin and 60 mg (0.34 mmol) of thiodipropionic acid, a molar ratio of 2.1:1, were placed in a 100 mL reactor. 40 mL acetonitrile was added to form a reaction mixture under nitrogen atmosphere. A catalytic amount of dehydrating agent concentrated sulfuric acid was added to the reaction system under magnetic stirring, and the reaction mixture was heated at 60° C. for 16 hours. When TLC indicated that the reaction was complete, heating was stopped and the protective device was removed. The reaction mixture was then concentrated under reduced pressure, and the concentrate was allowed to stand for stratification. The organic phase of the concentrated mixture was collected to obtain crude bergenin thiodipripionic acid ester. The crude product was further purified by using macroporous resin ADS-2 and methanol as an eluent. The eluent was repeatedly eluted, dried over anhydrous sodium sulfate, and s concentrated under reduced pressure to obtain 107.3 mg bergenin thiodipripionic acid ester, a yield of 39.5%.

Example 4

Preparation of Bergenin Thiodipripionic Acid Ester 338 mg (1.03 mmol) bergenin and 87 mg (0.49 mmol) of thiodipropionic acid, a molar ratio of 2.1:1, were placed in a 100 mL reactor. 40 mL tetrahydrofuran (THF) was added to form a reaction mixture under nitrogen atmosphere. A catalytic amount of dehydrating agent EDC was added to the reaction system under magnetic stirring, and the reaction mixture was heated at 60° C. for 16 hours. When TLC indicated that the reaction was complete, heating was stopped and the protective device was removed. The reaction mixture was then concentrated under reduced pressure, and the concentrate was allowed to stand for stratification. The organic phase of the concentrated mixture was collected to obtain crude bergenin thiodripionic acid ester. The crude product was further purified by using macroporous resin AB-8 and methanol as an eluent. The eluent was repeatedly eluted, dried over anhydrous sodium sulfate, and s concentrated under reduced pressure to obtain 152.4 mg bergenin thiodripionic acid ester, a yield of 38.9%.

Example 5

Preparation of bergenin thiodripionic acid ester 233 mg (0.71 Mmol) Bergenin and 60 mg (0.34 Mmol) of Thiodipropionic Acid, a molar ratio of 2.1:1, were placed in a 100 mL reactor. 40 mL THF was added to form a reaction mixture under nitrogen atmosphere. A catalytic amount of dehydrating agent DCC was added to the reaction system under magnetic stirring, and the reaction mixture was heated at 60° C. for 16 hours. When TLC indicated that the reaction was complete, heating was stopped and the protective device was removed. The reaction mixture was then concentrated under reduced pressure, and the concentrate was allowed to stand for stratification. The organic phase of the concentrated mixture was collected to obtain crude bergenin thiodipripionic acid ester. The crude product was further purified by using macroporous resin S-8 and methanol as an eluent. The eluent was repeatedly eluted, dried over anhydrous sodium sulfate, and s concentrated under reduced pressure to obtain 51.9 mg bergenin thiodipripionic acid ester, a yield of 19.1%.

Example 6

Preparation of Bergenin Thiodripripionic Acid Ester 338 mg (1.03 mmol) bergenin and 87 mg (0.49 mmol) of thiodipropionic acid, a molar ratio of 2.1:1, were placed in a 100 mL reactor. 40 mL THF was added to form a reaction mixture under nitrogen atmosphere. A catalytic amount of dehydrating agent concentrated sulfuric acid was added to the reaction system under magnetic stirring, and the reaction mixture was heated at 60° C. for 16 hours. When TLC indicated that the reaction was complete, heating was stopped and the protective device was removed. The reaction mixture was then concentrated under reduced pressure, and the concentrate was allowed to stand for stratification. The organic phase of the concentrated mixture was collected to obtain crude bergenin thiodipripionic acid ester. The crude product was further purified by using macroporous resin AB-8 and methanol as an eluent. The eluent was repeatedly eluted, dried over anhydrous sodium sulfate, and s concentrated under reduced pressure to obtain 114.1 mg bergenin thiodipripionic acid ester, a yield of 29.1%.

Example 7

Preparation of Bergenin Thiodripripionic Acid Ester 233 mg (0.71 mmol) bergenin and 60 mg (0.34 mmol) of thiodipropionic acid, a molar ratio of 2.1:1, were placed in a 100 mL reactor. 40 mL acetonitrile was added to form a reaction mixture under nitrogen atmosphere. A catalytic amount of dehydrating agent EDC was added to the reaction system under magnetic stirring, and the reaction mixture was heated at 60° C. for 16 hours. When TLC indicated that the reaction was complete, heating was stopped and the protective device was removed. The reaction mixture was then concentrated under reduced pressure, and the concentrate was allowed to stand for stratification. The organic phase of the concentrated mixture was collected to obtain crude bergenin thiodipripionic acid ester. The crude product was further purified by using macroporous resin AB-8 and methanol as an eluent. The eluent was repeatedly eluted, dried over anhydrous sodium sulfate, and s concentrated under reduced pressure to obtain 104.1 mg bergenin thiodipripionic acid ester, a yield of 38.3%.

Example 8

Preparation of Bergenin Thiodripripionic Acid Ester 338 mg (1.03 mmol) bergenin and 87 mg (0.49 mmol) of thiodipropionic acid, a molar ratio of 2.1:1, were placed in a 100 mL reactor. 40 mL acetonitrile was added to form a reaction mixture under nitrogen atmosphere. A catalytic amount of dehydrating agent EDC was added to the reaction system under magnetic stirring, and the reaction mixture was heated at 60° C. for 16 hours. When TLC indicated that the reaction was complete, heating was stopped and the protective device was removed. The reaction mixture was then concentrated under reduced pressure, and the concentrate was allowed to stand for stratification. The organic phase of the concentrated mixture was collected to obtain crude bergenin thiodipripionic acid ester. The crude product was further purified by using macroporous resin ADS-2 and methanol as an eluent. The eluent was repeatedly eluted, dried over anhydrous sodium sulfate, and s concentrated under reduced pressure to obtain 103.1 mg bergenin thiodipripionic acid ester, a yield of 26.3%.

Example 9

Preparation of Bergenin Thiodripripionic Acid Ester 233 mg (0.71 mmol) bergenin and 60 mg (0.34 mmol) of thiodipropionic acid, a molar ratio of 2.1:1, were placed in a 100 mL reactor. 40 mL THF was added to form a reaction mixture under nitrogen atmosphere. A catalytic amount of dehydrating agent EDC was added to the reaction system under magnetic stirring, and the reaction mixture was heated at 60° C. for 16 hours. When TLC indicated that the reaction was complete, heating was stopped and the protective device was removed. The reaction mixture was then concentrated under reduced pressure, and the concentrate was allowed to stand for stratification. The organic phase of the concentrated mixture was collected to obtain crude bergenin thiodipripionic acid ester. The crude product was further purified by using macroporous resin S-8 and methanol as an eluent. The eluent was repeatedly eluted, dried over anhydrous sodium sulfate, and s concentrated under reduced pressure to obtain 116.3 mg bergenin thiodipripionic acid ester, a yield of 42.8%.

Example 10

Preparation of Bergenin Thiodripripionic Acid Ester 338 mg (1.03 mmol) bergenin and 87 mg (0.49 mmol) of thiodipropionic acid, a molar ratio of 2.1:1, were placed in a 100 mL reactor. 40 mL THF was added to form a reaction mixture under nitrogen atmosphere. A catalytic amount of dehydrating agent EDC was added to the reaction system under magnetic stirring, and the reaction mixture was heated at 60° C. for 16 hours. When TLC indicated that the reaction was complete, heating was stopped and the protective device was removed. The reaction mixture was then concentrated under reduced pressure, and the concentrate was allowed to stand for stratification. The organic phase of the concentrated mixture was collected to obtain crude bergenin thiodipripionic acid ester. The crude product was further purified by using macroporous resin ADS-8 and methanol as an eluent. The eluent was repeatedly eluted, dried over anhydrous sodium sulfate, and s concentrated under reduced pressure to obtain 172 mg bergenin thiodipripionic acid ester, a yield of 43.9%.

Example 11

In the DPPH molecule, due to the presence of multiple electron-withdrawing —$NO_2$ and large π bonds of the benzene ring, nitrogen free radical is stabilized. Its methanol solution is purple and has a maximum absorption peak at 517 nm. After the addition of an antioxidant, DPPH captures an electron to be paired with the free electron, and the purple fades and turns into a yellow substance. The absorption at 517 nm disappears, and the degree of fading is quantitatively related to the number of electrons it captures. Based on this principle, a spectrophotometer is used to detect the change of the absorbance of the DPPH radical and the sample solution, and the ability of the sample to provide hydrogen atoms and scavenge free radicals can be measured.

Preparation of DPPH Solution: Measuring Exact Amount of 1,1-diphenyl-2-picryl hydrazyl (DPPH) and dissolving in methanol to prepare a 0.2 mmol/L DPPH Solution, Stored at 0° C. in Dark Preparation of sample solutions: Vitamin C (positive control), bergenin thiodipripionic acid ester (sample), bergenin (control), thiodipropionic acid (control), mixture of bergenin and thiodipropionic acid (control). The sample solution was serially diluted with acetonitrile, and four groups of controls were separately dissolved in a test tube with a certain amount of methanol to prepare the same concentration gradient as the sample. Four corresponding groups of control solutions were prepared in the same way. Gradient settings are shown in Table 1.

TABLE 1

Dilution gradient of the test solutions

| Numbering | Test solution | Concentration gradient/(mg/mL) |
|---|---|---|
| Vc | Vitamin C | 0.04, 0.08, 0.16, 0.83, 1.66, 8.28, 16.56, 24.84, 33.12 |
| B | Bergenin thiodipripionic acid ester | 0.04, 0.08, 0.16, 0.83, 1.66, 8.28, 16.56, 24.84, 33.12 |
| C | Bergenin | 0.04, 0.08, 0.16, 0.83, 1.66, 8.28, 16.56, 24.84, 33.12 |
| D | Thiodipripionic acid | 0.04, 0.08, 0.16, 0.83, 1.66, 8.28, 16.56, 24.84, 33.12 |
| E | Mixture of bergenin and thiodipropionic acid (2:1) | 0.04, 0.08, 0.16, 0.83, 1.66, 8.28, 16.56, 24.84, 33.12 |

Specific Steps:

Measuring the Scavenging Activity of the Sample Solutions:

2 mL of the sample solution (Table 1: B), 2 mL 0.2 mmol/L DPPH solution was added, the mixture was mixed and reacted at room temperature in dark for 30 minutes, and methanol was then added to adjust final volume. The absorbance Ai was measured at 517 nm. 2 mL control solution and 2 mL methanol were mixed, and the absorbance Aj was measured. 2 mL DPPH solution and 2 mL methanol were mixed, and the absorbance $A_0$ was measured.

Measuring the Scavenging Activity of the Control Solution:

2 mL of the control solutions (Table 1: C, D, E), 2 mL 0.2 mmol/L DPPH solution was added, the mixture was mixed and reacted at room temperature in dark for 30 minutes, and methanol was then added to adjust final volume. The absorbance Ai was measured at 517 nm. 2 mL control solution and 2 mL methanol were mixed, and the absorbance Aj was measured. 2 mL DPPH solution and 2 mL methanol were mixed, and the absorbance $A_0$ was measured. The scavenging activity of the sample solution and control solutions is calculated according to the following calculation formula.

$$\text{Scavenging activity (\%)} = [1-(Ai-Aj)/Ao]*100\%$$

The scavenging activity is shown in Table 3 and FIG. 1. In FIG. 1, the X axis represents the concentrations (mg/ml) of the sample and control solutions, and the Y axis represents the scavenging activity.

TABLE 2

Absorbance test result

| Sample | Absorbance | \multicolumn{9}{c}{Concentrations (mg/ml)} |
|---|---|---|---|---|---|---|---|---|---|---|
| | | 0.04 | 0.08 | 0.16 | 0.83 | 1.66 | 8.28 | 16.56 | 24.84 | 33.12 |
| B | Ai | 0.651 | 0.563 | 0.441 | 0.360 | 0.261 | 0.158 | 0.043 | 0.038 | 0.035 |
| | Aj | 0.003 | 0.003 | 0.003 | 0.002 | 0.003 | 0.001 | 0.004 | 0.004 | 0.001 |
| | Ao | | | | | 0.900 | | | | |
| C | Ai | 0.935 | 0.898 | 0.820 | 0.762 | 0.595 | 0.420 | 0.046 | 0.046 | 0.041 |
| | Aj | 0.003 | 0.003 | 0.002 | 0.003 | 0.002 | 0.003 | 0.003 | 0.003 | 0.002 |
| | Ao | | | | | 1.020 | | | | |
| D | Ai | 0.858 | 0.798 | 0.795 | 0.793 | 0.792 | 0.782 | 0.771 | 0.760 | 0.747 |
| | Aj | 0.004 | 0.003 | 0.003 | 0.002 | 0.003 | 0.003 | 0.003 | 0.003 | 0.002 |
| | Ao | | | | | 0.871 | | | | |
| E | Ai | 0.889 | 0.886 | 0.842 | 0.740 | 0.329 | 0.187 | 0.136 | 0.119 | 0.088 |
| | Aj | 0.003 | 0.004 | 0.004 | 0.002 | 0.002 | 0.004 | 0.003 | 0.003 | 0.003 |
| | Ao | | | | | 0.913 | | | | |

TABLE 3

Scavenging activity

| Concentrations | Scavenging activity/% (n = 3) | | | | |
|---|---|---|---|---|---|
| (mg/ml) | Vc | B | C | D | E |
| 0 | 0 | 0 | 0 | 0 | 0 |
| 0.04 | 94.90 | 28.01 | 8.63 | 1.96 | 2.96 |
| 0.08 | 94.90 | 37.78 | 12.25 | 8.73 | 3.40 |
| 0.16 | 95.03 | 51.33 | 19.80 | 9.07 | 8.21 |
| 0.83 | 95.03 | 60.22 | 25.59 | 9.18 | 19.17 |
| 1.66 | 98.67 | 76.33 | 41.86 | 9.41 | 64.14 |
| 8.28 | 98.92 | 82.56 | 59.12 | 10.56 | 79.85 |
| 16.56 | 99.00 | 95.67 | 94.78 | 11.83 | 85.43 |
| 24.84 | 99.00 | 96.22 | 94.87 | 13.09 | 87.29 |
| 33.12 | 99.00 | 96.22 | 95.18 | 14.47 | 90.69 |

As shown in Tables 1 to 3 and FIG. 1, bergenin thiodipripionic acid ester (B) showed a significant scavenging effect on DPPH in a concentration-dependent manner. Its DPPH clearance rate ranged from 28.01% (0.04 mg/mL) to 96.22% (33.12 mg/mL), comparing with a single bergenin (C), thiodipropionic acid (D), mixture of bergenin and thiodipropionic acid (2:1) (E), the scavenging ability of bergenin thiodipripionic acid ester (B) was significantly better at the same concentration. When the concentration reached 24.84 mg/mL, the scavenging effect of bergenin thiodipripionic acid ester (B) on DPPH is close to that of Vc, reaching 96.22%. The above experimental results show that bergenin thiodipripionic acid ester (B) has excellent antioxidant activity and can be used as a new type of antioxidant additive in food, medicine, and health care products.

Example 11

A method of improving the antioxidant property of *Ganoderma lucidum* spore oil using bergenin thiodipripionic acid ester Preparation of DPPH Solution: Measuring Exact Amount of 1,1-diphenyl-2-picryl hydrazyl (DPPH) and dissolving in methanol to prepare a 0.2 mmol/L DPPH Solution, Stored at 0° C. in Dark Preparation of sample solutions: anoderma lucidum spore oil (control), anoderma lucidum spore oil and 0.2% bergenin thiodipripionic acid ester (control), anoderma lucidum spore oil and 0.4% bergenin thiodipripionic acid ester (control), anoderma lucidum spore oil and 0.6% bergenin thiodipripionic acid ester (control), The sample solution was serially diluted with acetone, and three sets of controls were separately dissolved in a test tube with a certain amount of acetone to prepare the same concentration gradient as the sample. The corresponding three groups of control solutions were obtained. Gradient settings are shown in Table 4.

TABLE 4

Dilution gradient of the test solutions

| Numbering | Test solution | Concentration gradient/(mL/mL) |
|---|---|---|
| A | Anoderma lucidum spore oil | 3%, 4%, 5%, 6%, 7%, 8%, 9%, 10%, 11% |
| F | Anoderma lucidum spore oil and 0.2 % bergenin thiodipripionic acid ester | 3%, 4%, 5%, 6%, 7%, 8%, 9%, 10%, 11% |
| G | Anoderma lucidum spore oil and 0.4 % bergenin thiodipripionic acid ester | 3%, 4%, 5%, 6%, 7%, 8%, 9%, 10%, 11% |
| H | Anoderma lucidum spore oil and 0.6 % bergenin thiodipripionic acid ester | 3%, 4%, 5%, 6%, 7%, 8%, 9%, 10%, 11% |

Specific Steps:

Measuring the Scavenging Activity of the Sample Solutions:

2 mL of the sample solutions (Table 4: A), 2 mL 0.2 mmol/L DPPH solution was added, the mixture was mixed and reacted at room temperature in dark for 30 minutes, and methanol was then added to adjust final volume. The absorbance Ai was measured at 517 nm. 2 mL control solution and 2 mL methanol were mixed, and the absorbance Aj was measured. 2 mL DPPH solution and 2 mL acetone were mixed, and the absorbance $A_0$ was measured.

Measuring the Scavenging Activity of the Control Solution:

2 mL of the control solutions (Table 4: F, G, H), 2 mL 0.2 mmol/L DPPH solution was added, the mixture was mixed and reacted at room temperature in dark for 30 minutes, and methanol was then added to adjust final volume. The absorbance Ai was measured at 517 nm. 2 mL control solution and 2 mL methanol were mixed, and the absorbance Aj was measured. 2 mL DPPH solution and 2 mL acetone were mixed, and the absorbance $A_0$ was measured. The scavenging activity of the sample solution and control solutions is calculated according to the following calculation formula.

$$\text{Scavenging activity (\%)} = [1 - (A_i - A_j)/A_o] * 100\%$$

Figure 2:
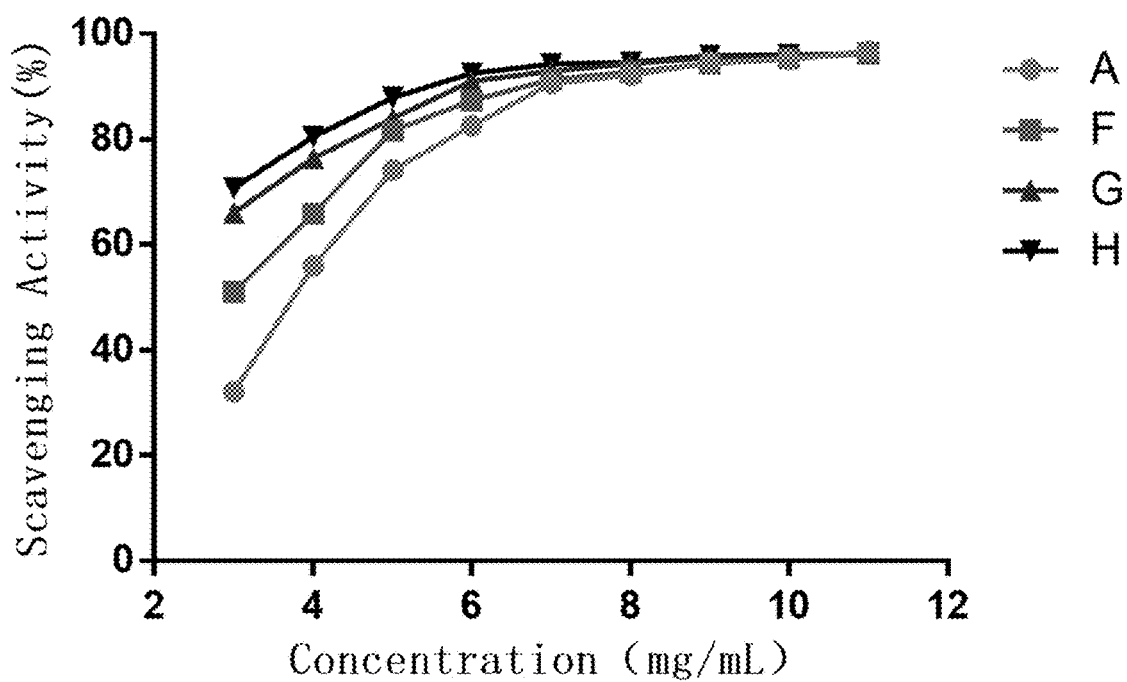
FIG. 2 shows the scavenging activity of the samples A, F, G, and H at different concentrations.

The scavenging activity is shown in Table 6 and FIG. 2. In FIG. 2, the X axis represents the concentrations (mg/ml) of the sample and control solutions, and the Y axis represents the scavenging activity.

TABLE 5

Absorbance test result

| Sample | Absorbance | Concentrations (mg/ml) | | | | | | | | |
|---|---|---|---|---|---|---|---|---|---|---|
| | | 3% | 4% | 5% | 6% | 7% | 8% | 9% | 10% | 11% |
| A | Ai | 0.895 | 0.594 | 0.381 | 0.262 | 0.183 | 0.142 | 0.112 | 0.106 | 0.090 |
| | Aj | 0.024 | 0.021 | 0.025 | 0.039 | 0.043 | 0.045 | 0.044 | 0.044 | 0.048 |
| | Ao | | | | | 1.284 | | | | |
| F | Ai | 0.502 | 0.351 | 0.189 | 0.132 | 0.092 | 0.076 | 0.061 | 0.050 | 0.041 |
| | Aj | 0.003 | 0.003 | 0.004 | 0.004 | 0.003 | 0.003 | 0.003 | 0.003 | 0.004 |
| | Ao | | | | | 1.019 | | | | |

TABLE 5-continued

| | | Absorbance test result | | | | | | | | |
|---|---|---|---|---|---|---|---|---|---|---|
| | | Concentrations (mg/ml) | | | | | | | | |
| Sample | Absorbance | 3% | 4% | 5% | 6% | 7% | 8% | 9% | 10% | 11% |
| G | Ai | 0.349 | 0.244 | 0.166 | 0.094 | 0.075 | 0.060 | 0.049 | 0.046 | 0.042 |
| | Aj | 0.004 | 0.003 | 0.003 | 0.004 | 0.003 | 0.003 | 0.003 | 0.004 | 0.004 |
| | Ao | | | | | 1.019 | | | | |
| H | Ai | 0.302 | 0.201 | 0.126 | 0.084 | 0.064 | 0.058 | 0.046 | 0.044 | 0.042 |
| | Aj | 0.003 | 0.004 | 0.003 | 0.004 | 0.002 | 0.004 | 0.004 | 0.003 | 0.003 |
| | Ao | | | | | 1.019 | | | | |

TABLE 6

| | Scavenging activity | | | |
|---|---|---|---|---|
| Concentrations | Scavenging activity/% (n = 3) | | | |
| (mg/ml) | A | F | G | H |
| 3% | 32.16% | 51.05% | 66.05% | 70.67% |
| 4% | 55.99% | 65.85% | 76.39% | 80.56% |
| 5% | 74.14% | 81.73% | 84.01% | 87.96% |
| 6% | 82.63% | 87.37% | 91.01% | 92.51% |
| 7% | 90.63% | 91.36% | 92.93% | 94.29% |
| 8% | 92.21% | 92.83% | 94.40% | 94.61% |
| 9% | 94.54% | 94.41% | 95.58% | 95.87% |
| 10% | 95.17% | 95.39% | 95.87% | 96.07% |
| 11% | 96.73% | 96.36% | 96.27% | 96.27% |

As shown in Table 4-6 and FIG. 2, the clearance rate of DPPH by *Ganoderma lucidum* spore oil (A) at a concentration of 2% was 32.13%. 2% *Ganoderma lucidum* spore oil with 0.2% bergenin thiodipripionic acid ester (F), 0.4% bergenin thiodipripionic acid ester (G), and 0.6% bergenin thiodipripionic acid ester (H) have DPPH clearance rate of 51.05%, 66.05%, and 70.67%, respectively. Bergenin thiodipripionic acid ester improves the antioxidant capacity of *Ganoderma lucidum* spore oil, and has a significant dose-effect relationship with the added concentration. The above experimental results show that bergenin thiodipripionic acid ester can be used as a new type of antioxidant additive in the fields of food, medicine and health care products to improve and extend the shelf life of the products.

What is claimed is:

1. A compound having the following formula (I):

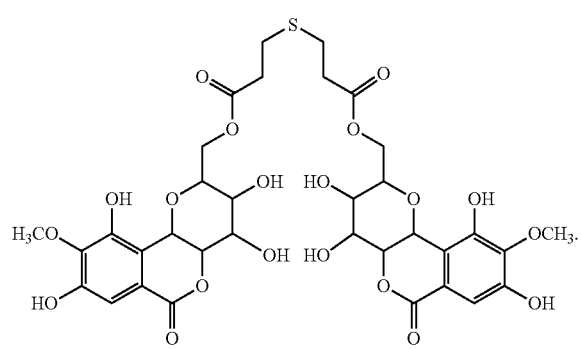

2. A method of preparing the compound of claim 1, comprising:
reacting a compound of formula (II) with a compound of formula (III) to obtain the compound of formula (I):

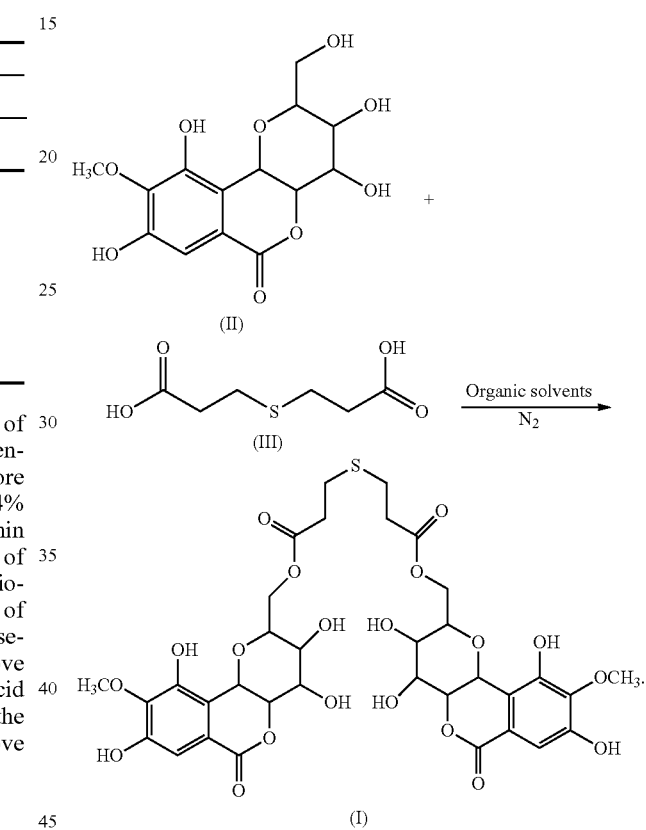

3. The method of claim 2, wherein the reaction of the compound of formula (II) with the compound of formula (III) comprises the following steps:
placing the compound of formula (II) and the compound of formula (III), in a molar ratio of 2:1 to 2.2:1, in a reactor under nitrogen atmosphere to obtain a reaction mixture;
adding an organic solvent and a certain amount of a dehydrating agent to the reaction mixture under magnetic stirring;
heating the reaction mixture at 50-60° C. for 15-17 hours;
concentrating the reaction mixture to obtain crude compound of the formula (I); and
using a macroporous resin to purify the crude compound of the formula (I) to obtain the compound of formula (I).

4. The method of claim 3, wherein the organic solvent is acetonitrile or THF.

5. The method of claim 4, wherein the organic solvent is acetonitrile.

6. The method of claim 3, wherein the molar ratio of the compound of formula (II) and the compound of formula (III) is 2.2:1.

7. The method of claim 3, wherein the dehydrating agent is DCC, concentrated sulfuric acid, or EDC.

8. The method of claim 7, wherein the dehydrating agent is EDC.

9. The method of claim 3, wherein the reaction mixture is heated at 60° C.

10. The method of claim 3, wherein the reaction mixture is heated for 16 hours.

11. The method of claim 3, wherein the macroporous resin is an AB-8 type polar macroporous resin, an S-8 type polar macroporous resin, or an ADS-2 type polar macroporous resin.

12. The method of claim 11, wherein the macroporous resin is an AB-8 type polar macroporous resin.

* * * * *